US012655091B2

(12) United States Patent
Bastida Codina et al.

(10) Patent No.: US 12,655,091 B2
(45) Date of Patent: Jun. 16, 2026

(54) N-BENZYL-ALPHA-AMINOAMIDES AS ANAPHASE-PROMOTING COMPLEX/CYCLOSOME (APC/C) INHIBITORS

(71) Applicants: CONSEJO SUPERIOR DE INVESTIGACIONES CIENTÍFICAS (CSIC), Madrid (ES); OXFORD BROOKES UNIVERSITY, Oxford (GB)

(72) Inventors: Agatha Bastida Codina, Madrid (ES); Raúl Benito Arenas, Madrid (ES); Victor M. Bolanos-García, Oxford (GB); Natalie Laura Curtis, Oxford (GB)

(73) Assignees: CONSEJO SUPERIOR DE INVESTIGACIONES CIENTÍFICAS (CSIC), Madrid (ES); OXFORD BROOKES UNIVERSITY, Oxford (GB)

( * ) Notice: Subject to any disclaimer, the term of this patent is extended or adjusted under 35 U.S.C. 154(b) by 416 days.

(21) Appl. No.: 18/267,330

(22) PCT Filed: Dec. 16, 2021

(86) PCT No.: PCT/EP2021/086290
§ 371 (c)(1),
(2) Date: Jun. 14, 2023

(87) PCT Pub. No.: WO2022/129397
PCT Pub. Date: Jun. 23, 2022

(65) Prior Publication Data

US 2024/0043374 A1 Feb. 8, 2024

(30) Foreign Application Priority Data

Dec. 16, 2020 (EP) .................................... 20383100

(51) Int. Cl.
*C07C 237/20* (2006.01)
*A61K 31/165* (2006.01)
(Continued)

(52) U.S. Cl.
CPC .......... *C07C 237/20* (2013.01); *A61K 31/165* (2013.01); *A61K 31/27* (2013.01);
(Continued)

(58) Field of Classification Search
CPC ... C07C 237/20; C07C 237/06; A61K 31/165; A61K 31/27; A61P 35/00
See application file for complete search history.

(56) References Cited

U.S. PATENT DOCUMENTS

| | | | |
|---|---|---|---|
| 2004/0106794 A1 | 6/2004 | Taveras et al. | |
| 2013/0230458 A1 | 9/2013 | King et al. | |

FOREIGN PATENT DOCUMENTS

| | | | |
|---|---|---|---|
| WO | WO-2005082343 A2 * | 9/2005 | .............. A61P 37/00 |
| WO | 2012031118 A2 | 3/2012 | |

(Continued)

OTHER PUBLICATIONS

Amber M. King, "Primary Amino Acid Derivatives: Substitution of the 40-N0-Benzylamide Site in (R)-N0-Benzyl 2-Amino-3-methylbutanamide, (R)-N0-Benzyl 2-Amino-3,3-dimethylbutanamide, and (R)-N0-Benzyl 2-Amino-3-methoxypropionamide Provides Potent Anticonvulsants with Pain-Attenuating Properties", Journal, 2011, p. 6417-6431, vol. 54, No. 19, Journal of Medicinal Chemistry.

(Continued)

*Primary Examiner* — Savitha M Rao
*Assistant Examiner* — Elena V Vishnyakova
(74) *Attorney, Agent, or Firm* — Hayes Soloway PC

(57) ABSTRACT

The invention relates to a compound of formula I which are inhibitors of anaphase promoting complex/cyclosome
(Continued)

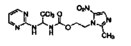

apcin

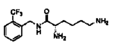
o-TFB-Lys

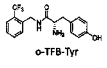
o-TFB-Tyr

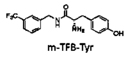
m-TFB-Tyr p-TFB-Tyr (APC/C) function of formula I, wherein the meaning for $R_1$ and $R_2$ is as disclosed in the description. These compounds are useful in the treatment of cancer, particularly, in the treatment of breast cancer.

Formula I

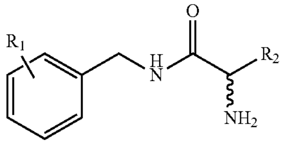

10 Claims, 9 Drawing Sheets

(51) Int. Cl.
*A61K 31/27* (2006.01)
*A61P 35/00* (2006.01)
*C07C 237/06* (2006.01)

(52) U.S. Cl.
CPC ............ *A61P 35/00* (2018.01); *C07C 237/06* (2013.01); *C07B 2200/09* (2013.01)

(56) References Cited

FOREIGN PATENT DOCUMENTS

| | | | |
|---|---|---|---|
| WO | 2012149266 | A1 | 11/2012 |
| WO | 2020210032 | A1 | 10/2020 |

OTHER PUBLICATIONS

Di Fiore B. et al., "The ABBA Motif Binds APC/C Activators and is Shared by APC/C Substrates and Regulators", Journal, 2015, p. 358-372, vol. 32, Developmental Cell.

C.H. Golias, "Cell Proliferation and Cell Cycle Control: a Mini Review", Journal, 2004, p. 1134-1141, vol. 58, Int. J. Clin. Pract.

Nugent R. et al., "I-H-11: Innovative therapy to halt proliferation of high mortality cancer tumour cells", Report, 2021, p. 1-11, iCure Cohort H Patent Insights Report—Mathys & Squire Consulting.

Izawa D., "The mitotic checkpoint complex binds a second CDC20 to inhibit active APC/C", Journal, 2014, p. 631-634, vol. 517, Nature.

Meadows, JC et al., "Sharpening the anaphase switch", Journal, 2015, p. 19-22, vol. 43, Biochemical Society Transactions.

Yau, Mei-Kwan et al., "Benzylamide antagonists of protease activated receptor 2 with anti-inflammatory activity", Journal, 2015, p. 986-991, vol. 26, No. 3, Bioorganic & Medicinal Chemistry Letters.

Najda-Mocarska, Ewelina et al., "New thiourea organocatalysts and their application for the synthesis of 5-(1H-indol-3-yl)methyl-2,2-dimethyl-1,3-dioxane-4,6-diones a source of chiral 3-indoylmethyl ketenes", Journal, 2017, p. 14-25, vol. 48, No. 1, Synthetic Communications.

Wang, Tzu-Hao et al., "Paclitaxel-Induced Cell Death", Journal, 2000, p. 2619-2628, vol. 88, No. 11, Cancer 1.

Wang, Lixia et al., "Targeting Cdc20 as a novel cancer therapeutic strategy", Author Manuscript, 2015, p. 141-151, vol. 151, Pharmacol Ther.

Zich, Judith et al., "Getting down to the phosphorylated 'nuts and bolts' of spindle checkpoint signalling", Journal, 2010, p. 18-27, vol. 35, No. 1, Trends in Biochemical Sciences.

* cited by examiner apcin o-TFB-Lys o-TFB-Tyr m-TFB-Tyr p-TFB-Tyr

N-BENZYL-ALPHA-AMINOAMIDES AS ANAPHASE-PROMOTING COMPLEX/CYCLOSOME (APC/C) INHIBITORS

CROSS-REFERENCE TO RELATED APPLICATIONS AND PRIORITY

This patent application claims priority from PCT Application No. PCT/EP2021/086290 filed Dec. 16, 2021, which claims priority from European Patent Application No. 20383100.3 filed Dec. 16, 2020.

The invention relates to a compound of formula I which are inhibitors of anaphase promoting complex/cyclosome (APC/C) and to a pharmaceutical composition thereof for it use in the treatment of cancer, particularly, in the treatment of breast cancer. Moreover, the invention relates to a composition of a compound of formula I administered in combination with proTAME.

BACKGROUND ART

Cancer is a disease that affects many people and is a leading cause of death in humans. Cancer is, in part, characterized by uncontrolled cellular proliferation (see Golias, C H., Charalabopoulos, A., Charalabopoulos, K. Cell proliferation and cell cycle control: a mini review. *Int J Clin Pract,* 2004, 58, 12, 1134-1141). Hence, compounds that disrupt cell division (e.g., mitosis) can be part of a cancer chemotherapy armament. For example, some current mitotic disrupters in clinical use, such as paclitaxel, appear to target microtubules and thus can disrupt mitotic spindle function (see Wang, T-H., Hsin-Shih Wang, MD., Soong, YK. Paclitaxel-Induced Cell Death. Cancer 1, 2000, 88 (11)). Indeed, prolonged mitotic disruption may cause cells to undergo apoptosis. However, some tumors develop resistance to microtubule disrupting drugs by inactivation of the spindle assembly checkpoint (SAC), a highly intricate signaling network orchestrated by some proteins as the protein Cdc20 that ensures the accurate and timely segregation of chromosomes during cell division. Recruitment of SAC proteins to the kinetochore, the site for attachment of chromosomes to microtubule polymers that pull sister chromatids apart during cell division, is essential for full activity and optimal function of the SAC. Cdc20 binding to BubR1 mediates the recruitment of Cdc20 to the kinetochore whereas Cdc20 binding to the Anaphase Promoting Complex/Cyclosome (APC/C) regulates the interaction of APC/C with specific ubiquitin substrates for their subsequent degradation by the proteasome during cell cycle progression, thus governing cell cycle forward in a unidirectional manner (see Meadows J C, Millar J B. Sharpening the anaphase switch. *Biochem Soc Trans* 2015, 43:19-22; Izawa D, Pines J. The mitotic checkpoint complex binds a second CDC20 to inhibit active APC/C. Nature 2015, 517: 631-34; Di Fiore B. et al. The ABBA motif binds APC/C activators and is shared by APC/C substrates and regulators. Dev Cell 2015, 32:358-72; Zich J, Hardwick K G. Getting down to the phosphorylated ‘nuts and bolts’ of spindle checkpoint signalling. *Trends Biochem Sci.* 2010, 35:18-27; and WO 2012/149266). To enable the development of more effective therapeutic approaches against breast tumors will be necessary to develop new chemical inhibitors that affect Cdc20 protein-protein interactions important for SAC function, including APC/C regulation, in cancer cells where Cdc20 is abnormally overproduced and also in tumours associated with aberrant SAC signaling and with chromosome segregation defects. Cdc20 protein can function as an oncoprotein to promote the development of breast cancers. To date only the compound Apcin in combination with ProTAME is a target of Cdc20 as a cancer therapeutic strategy (see Lixia Wanga, Jinfang Zhangb, Lixin Wanb, Xiuxia Zhoua, Zhiwei Wanga, Wenyi Wei. Targeting Cdc20 as a novel cancer therapeutic strategy. *Pharmacol Ther.* 2015; 151: 141-151; PCTUS2011050203; and US 2013/0230458). Apcin (APC/C inhibitor), binds Cdc20 and prevents APC/C substrate recognition, thereby inhibiting APC/C substrate ubiquitination.

Thus, there is a need to dispose of new inhibitors of APC/C for the treatment of cancer and, particularly, for the treatment of breast cancer.

SUMMARY OF THE INVENTION

A first aspect of the present invention related to a compound of formula I:

Formula I

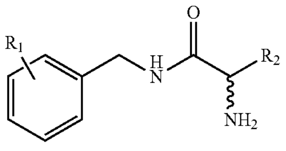

or a pharmaceutical salt thereof, wherein:

$R_1$ represents H, aryl, $C_1$-$C_{20}$ alkyl, —$CF_3$, $CCl_3$ or —$CBr_3$;

$R_2$ represents $C_1$-$C_6$ alkyl optionally substituted by —$NH_2$— or $Cy_1$;

$Cy_1$ represents a phenyl group (-Ph) optionally substituted by —OH.

Accordingly, the compounds of formula I may be free or in form of salt. Examples of anions of the salts of the compounds of formula I include, among others, anion chloride ($Cl^-$) and anion TFA ($CF_3CO_2^-$).

Some compounds of formula I can have chiral centers that can give rise to various stereoisomers. The present invention relates to each of these stereoisomers and also mixtures thereof.

The group $R_1$ of the compounds of formula I can be in any of the available ortho-, meta- or para-positions.

In another embodiment, the invention relates to the compound of formula I as defined above, wherein $Cy_1$ represents a phenyl group (-Ph) substituted by —OH in para-position.

In another embodiment the invention relates to the compound of formula I as defined above, wherein R, is —$CF_3$, $CCl_3$ or —$CBr_3$, and preferably wherein R, is —$CF_3$.

In another embodiment the invention relates to the compound of formula I as defined above, wherein $R_2$ is $C_1$-$C_4$ alkyl substituted by —$NH_2$.

In another embodiment the invention relates to the compound of formula I as defined above, wherein $R_2$ is a group of formula $R_2$-a:

$R_2$-a

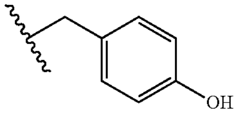

In another embodiment the invention relates to the compound of formula I as defined above, wherein $R_2$ is a group of formula $R_2$-b:

$R_2$-b

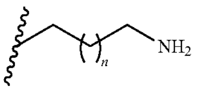

In another embodiment, the invention relates to the compound of formula I as defined above, wherein the compound of formula I is selected from:

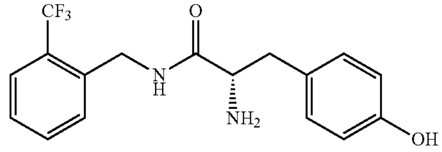

o-TFB-Tyr

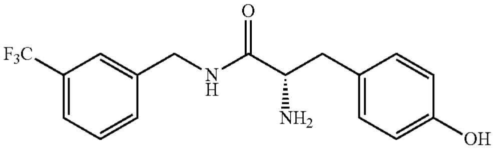

m-TFB-Tyr

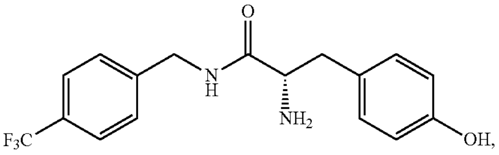

and p-TFB-Tyr

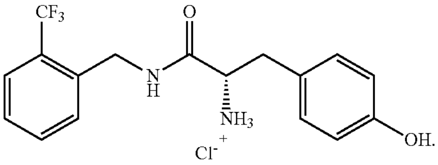

o-TFB-Tyr-Cl

In another embodiment, the invention relates to the compound of formula I as defined above, wherein the compound of formula I is selected from:

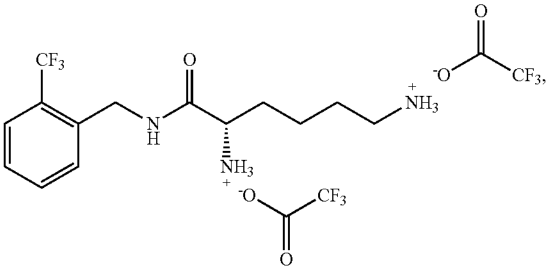

o-TFB-Lys-TFA

-continued

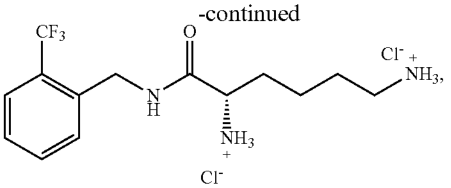

and o-TFB-Lys-Cl

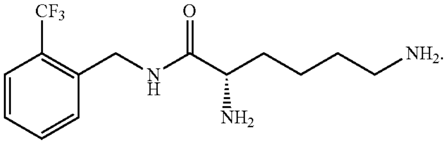

o-TFB-Lys

Another aspect of the invention relates to a pharmaceutical composition which comprises a compound of formula I as defined above or a pharmaceutically acceptable salt thereof and one or more pharmaceutically acceptable excipients.

The compound of formula I or a pharmaceutically acceptable salt thereof can be administered alone or in combination with a prodrug, said prodrug is preferably pro-N-4-tosyl-L-arginine methyl ester (proTame).

Accordingly, another aspect of the invention relates to a pharmaceutical composition comprising a compound of formula I as defined above, in combination with a further compound selected from pro-N-4-tosyl-L-arginine methyl ester (proTame).

Another aspect of the invention relates to a compound of formula I or a pharmaceutically acceptable salt thereof, for use in therapy.

Another aspect of the invention relates to a compound of formula I:

Formula I

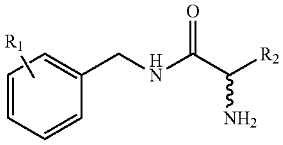

wherein:

$R_1$ represents H, aryl, $C_1$-$C_{20}$ alkyl, —$CF_3$, $CCl_3$, —$CBr_3$ or —$CI_3$;

$R_2$ represents $C_1$-$C_6$ alkyl optionally substituted by —$NH_2$ or $Cy_1$;

$Cy_1$ represents a phenyl group (-Ph) optionally substituted by —OH, for use in the treatment of cancer.

In another embodiment the invention relates to the compound of formula I for the use as defined above, wherein the compound of formula I is selected from:

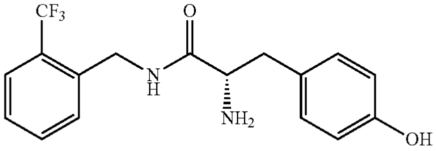

o-TFB-Tyr

-continued

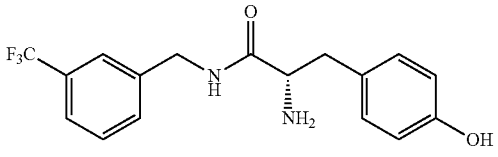

m-TFB-Tyr

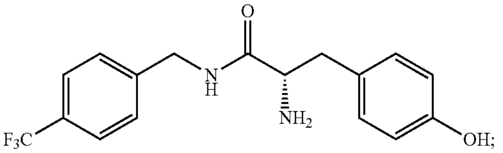

and m-TFB-Tyr

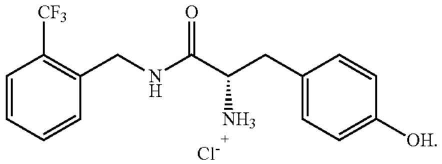

o-TFB-Tyr-Cl

In another embodiment the invention relates to the compound of formula I for the use as defined above, wherein the compound of formula I is selected from:

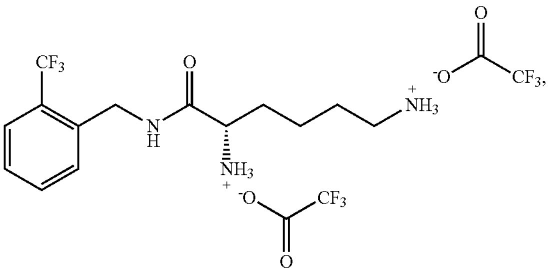

o-TFB-Lys-TFA

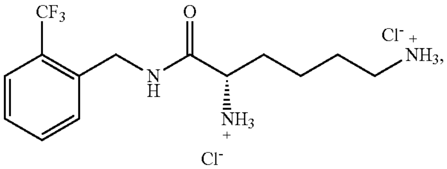

and o-TFB-Lys-Cl

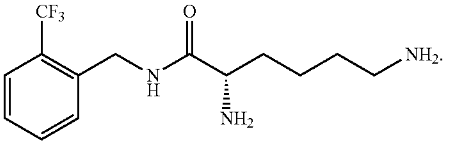

o-TFB-Lys

In another embodiment the invention relates to the compound of formula I for the use as defined above, for the treatment of breast cancer.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

EXAMPLES

Computing

Figure 1:
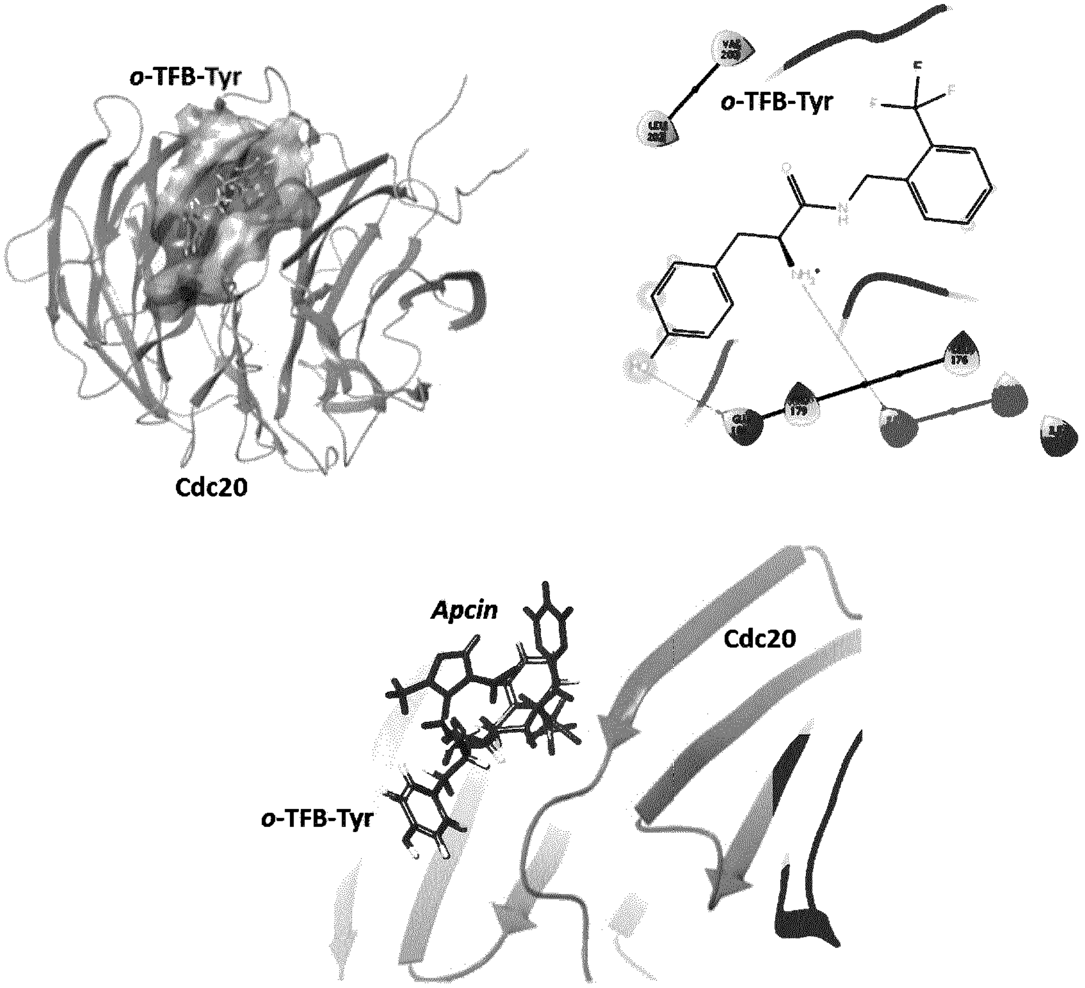
FIG. 1. Shows 3D structure of the complex Cdc20-o-TFB-Tyr, contacts o-TFB-Tyr Cdc20 and complex Apcin, o-TFB-Tyr-Cdc20.

Technique for docking (Maestro Suite, Schrodinger) flexible ligands with chemical structure I into the binding sites of Cdc20 protein (rigid) is presented. (FIG. 1) The method is based on a pre-generated set of conformations for the compounds (o-, m-, p-TFB-aa, ligand) and a final flexible gradient-based optimization of the ligand in the binding site of the protein. The receptor binding site is defined as a cubic box and places the compound in the centre of the binding pocket. For all cases, the box is large enough to guarantee independence of the docking results from binding site definitions. The docking parameters (score docking kcal/mol) give an idea of the best complex compound-protein.

Synthesis of o-, m- or p-Trifluorobenzyl L-Aminoacid Derivatives (o-TFB-Tyr, o-TFB-Lys and m-TFB-Tyr, p-TFB-Tyr).

1. Protecting of Amino Group of L-Aminoacid with t-Butoxycarbonyl Group:

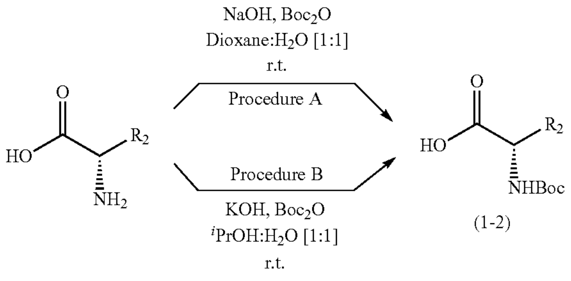

(1-2)

L-aminoacid was suspended in a 1:1 mixture of water and dioxane (procedure A) or 2-propanol (procedure B) under argon. After, sodium hydroxide (procedure A) or potassium hydroxide (procedure B) in water was added under constant stirring. After di-tert-butylcarbonate addition, the reaction was stirred at room temperature. When the reaction finished, the solvent was removed at reduced pressure until a half of the volume and then potassium hydrogen sulfate added until the solution was brought to pH=2. The reaction solution was extracted with ethyl acetate and the organic phase washed with saturated sodium chloride solution and water. The solution was dried over sodium sulfate and then filtered. The filtrate was concentrated to dryness. We used the product in next reaction without further purification.

| Aminoacid | | Procedure | Yield |
|---|---|---|---|
| Lys | 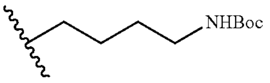 (1) | A | 87% |
| Tyr | 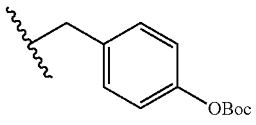 (2) | B | 93% |

2. Coupling Reaction of Boc-L-Aminoacids and Trifluorobenzylamine 2.1. Using 2-Trifluorobenzylamine as Coupling Reagent

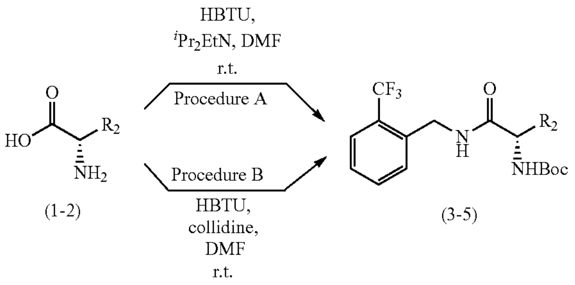

(1-2) (3-5)

Boc-L-aminoacid was dissolved in dry DMF under argon. After this, diisopropylethylamine (procedure A) or 2,4,6-collidine (procedure B) and HBTU were added sequentially at room temperature (r.t.) and stirred for 30 min. Then, trifluorobenzylamine was added at r.t. and the reaction was stirred overnight at r. t. When the reaction was completed the solvent was removed under reduced pressure. The crude product was then purified by silica-gel chromatography.

| Aminoacid | | Procedure | Yield (%) |
|---|---|---|---|
| Lys | 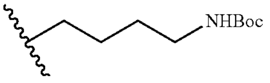 (3) | A | 72% |
| Tyr | 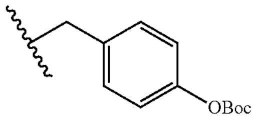 (4) | B | 33% |
| | 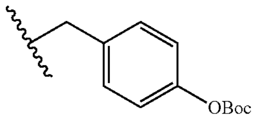 (5) | | 67% |

(2S)-2,6-bis[(tert-butoxycarbonyl)amino]-N-[2-(trifluoromethyl)benzyl]hexanamide (3)

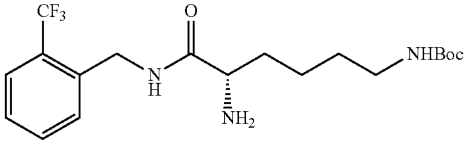

(3)

$^1$H-NMR (500 MHz, $CDCl_3$): δ 7.63 (1H, d, J=7.5 Hz), 7.54-4.47 (2H, m), 7.36 (1H, t, J=7.5 Hz), 6.65 (1H, b.s.), 5.17 (1H, b.s.), 4.65-4.56 (2H, m), 4.07 (1H, b.s.), 3.09 (2H, m), 1.89-1.81 (1H, m), 1.69-1.59 (1H, m), 1.53-1.44 (2H, m), 1.42 (9H, s), 1.40 (9H, s), 1.40-1.39 (2H, m) ppm. $^{13}$C-NMR (125 MHz, $CDCl_3$): δ 172.1, 156.2, 155.8, 136.4, 132.3, 130.1, 128.0 (q, J=30.9 Hz), 127.5, 125.9 (q, J=5.8 Hz), 124.4 (q, J=273.9 Hz), 80.2, 79.2, 54.6, 39.9 (q, J=2.5 Hz), 39.7, 31.5, 29.7, 28.4, 28.2, 22.6 ppm. LRMS (ESI-ES$^+$): m/z 504 $(M+H)^+$, 526 $(M+Na)^+$. IR (KBr): ν 3318, 3080, 2978, 2934, 2867, 1693, 1610, 1525, 1457, 1392, 1367, 1315, 1250, 1166, 1121, 1059, 1039, 867, 769, 655 $cm^{-1}$.

(2S)-2-[(tert-butoxycarbonyl)amino]-3-{4-[(tert-butoxycarbonyl)hydroxy]phenyl}-N-[2-(trifluoromethyl)benzyl]propanamide (4)

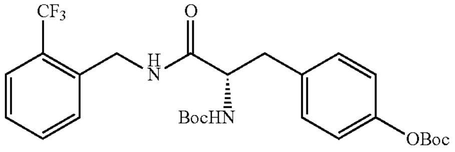

(4)

$^1$H-NMR (500 MHz, $CDCl_3$): δ 7.60 (1H, d, J=7.6 Hz), 7.47 (1H, t, J=7.8 Hz), 7.37-7.30 (2H, m), 7.14 (2H, d, J=8.4 Hz), 7.03 (2H, d, J=8.4 Hz), 6.34 (1H, b.s.), 5.03 (1H, b.s.), 4.57 (1H, dd, J=15.6, 6.4 Hz), 4.52 (1H, dd, J=15.6, 6.4 Hz), 4.34 (1H, b.s.), 3.11-3.00 (2H, m), 1.55 (9H, s), 1.38 (9H, s) ppm. $^{13}$C-NMR (125 MHz, $CDCl_3$): δ 171.0, 155.4, 151.8, 150.0, 136.1, 133.9, 132.2, 130.2, 130.1, 128.0 (q, J=31.3 Hz), 127.5, 125.9 (q, J=6.5 Hz), 124.3 (q, J=274.0 Hz), 121.4, 83.6, 80.4, 55.8, 39.9, 37.4, 28.2, 27.7 ppm. LRMS (EI): m/z 538 (M+, 0.1), 321 (100), 231 (6), 159 (22), 136 (21)

(2S)-2-[(tert-butoxycarbonyl)amino]-3-[4-(hydroxy)phenyl]-N-[2-(trifluoromethyl) benzyl]propanamide (5)

(5)

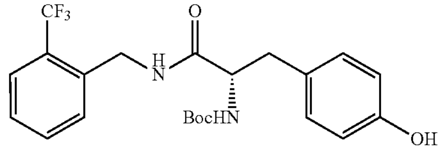

$^1$H-NMR (400 MHz, $CDCl_3$): δ 7.58 (1H, d, J=7.6 Hz), 7.43 (1H, t, J=7.6 Hz), 7.32 (1H, t, J=7.6 Hz), 7.22 (1H, b.s.), 6.93 (2H, d, J=8.1 Hz), 6.66 (2H, d, J=8.1 Hz), 6.41 (1H, t, J=6.2 Hz), 5.19 (1H, b.s.), 4.59 (1H, dd, J=15.4, 6.1 Hz), 4.46 (1H, dd, J=15.5, 5.6 Hz), 4.31 (1H, b.s.), 2.97 (1H, J=14.3, 6.5 Hz), 2.92 (1H, dd, J=14.3, 7.8 Hz), 1.39 (9H, s) ppm. $^{13}$C-NMR (100 MHz, $CDCl_3$): δ 171.5, 155.6, 155.1, 135.9, 132.2, 130.3, 130.0 (q, J=3.3 Hz), 127.9 (q, J=29.7 Hz), 127.8, 127.5, 125.8 (q, J=5.1 Hz), 124.3 (q, J=274.3 Hz), 115.6, 80.6, 56.2, 39.9, 37.5, 28.2 ppm. LRMS (EI): m/z 438 (M+, 0.5), 321 (100), 231 (5).

2.2. Using 3- or 4-Trifluorobenzylamine as Coupling Reagents

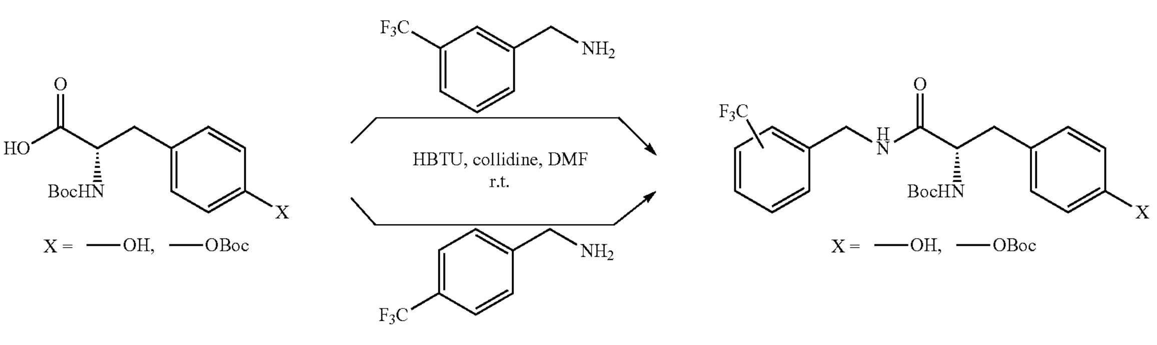

Boc-L-tyrosine was dissolved in dry DMF under argon. After this, 2,4,6-collidine and HBTU were added sequentially at r.t. and stirred for 30 min. Then, 3-trifluorobenzylamine (procedure A) or 4-trifluorobenzylamine (procedure B) was added at r.t. and the reaction stirred overnight at r. t. When the reaction was completed, the solvent was removed under reduced pressure. The crude product was purified by silica-gel chromatography.

| Aminoacid | Procedure | | X = | Yield (%) |
|---|---|---|---|---|
| Tyr | A | 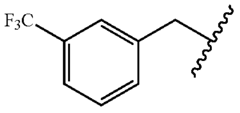 [SMILES: *Cc1cccc(C(F)(F)F)c1] | OBoc (6)<br>OH (7) | 14%<br>59% |
| | B | 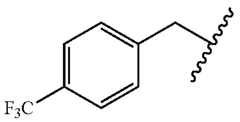 | OBoc (8)<br>OH (9) | 52%<br>39% |

(2S)-2-[(tert-butoxycarbonyl)amino]-3-{4-[(tert-butoxycarbonyl)hydroxy]phenyl}-N-[3-(trifluoromethyl)benzyl]propanamide (6)

(6)

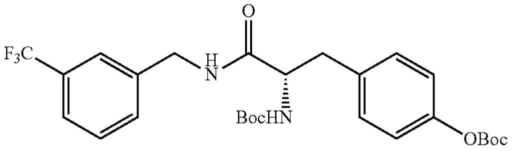

$^1$H-NMR (500 MHz, $CDCl_3$): δ 7.48 (1H, d, J=7.5 Hz), 7.43 (1H, s), 7.61 (1H, t, J=7.5 Hz), 7.27 (1H, b.s.), 7.15 (2H, d, J=8.3 Hz), 7.04 (2H, d, J=8.3 Hz), 6.58 (1H, b.s.), 5.16 (1H, b.s.), 4.36 (3H, s), 3.05 (2H, s), 1.54 (9H, s), 1.36 (9H, s) ppm. $^{13}$C-NMR (125 MHz, $CDCl_3$): δ 171.3, 155.5, 151.8, 150.0, 138.8, 134.0, 130.9, 130.7 (q, J=32.9 Hz), 130.2, 129.1, 124.3, 124.2, 123.9 (q, J=271.3 Hz), 121.4, 83.5, 80.4, 55.8, 42.9, 37.6, 28.2, 27.6 ppm. LRMS (EI): m/z 321 (100), 231 (6), 159 (34), 136 (22).

(2S)-2-[(tert-butoxycarbonyl)amino]-3-[4-(hydroxy) phenyl]-N-[3-(trifluoromethyl) benzyl] propanamide (7)

(7)

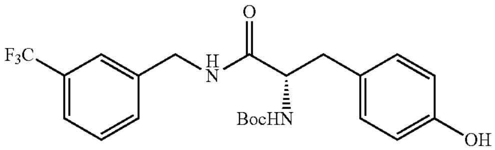

$^1$H-NMR (500 MHz, $CDCl_3$): δ 7.92 (1H, b.s.), 7.47 (1H, d, J=7.7 Hz), 7.41 (1H, s), 7.36 (1H, t, J=7.7 Hz), 7.20 (1H, b.s.), 6.97 (1H, b.s.), 6.95 (2H, d, J=8.4 Hz), 6.65 (2H, d, J=8.4 Hz), 5.38 (1H, b.s.), 4.38 (1H, dd, J=15.5, 5.2 Hz), 4.31 (1H, dd, J=15.5, 5.6 Hz), 4.24 (1H, q, J=7.1 Hz), 2.91

(2H, d, J=7.1 Hz), 1.36 (9H, s) ppm. $^{13}$C-NMR (125 MHz, $CDCl_3$): δ 171.9, 155.7, 155.4, 138.7, 130.9 (×2C), 130.3, 129.0, 127.4, 124.2, 124.1 (q, J=3.1 Hz), 123.9 (q, J=272.3 Hz), 115.4, 80.4, 56.1, 42.8, 37.7, 28.1 ppm. LRMS (EI): m/z 438 (M+, 0.3), 321 (100), 231 (3), 159 (54), 136 (24).

(2S)-2-[(tert-butoxycarbonyl)amino]-3-{4-[(tert-butoxycarbonyl)hydroxy]phenyl}-N-[4-(trifluoromethyl)benzyl]propanamide (8)

(8)

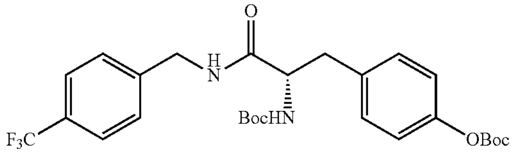

$^1$H-NMR (300 MHz, $CDCl_3$): δ 7.55 (2H, d, J=8.1 Hz), 7.20 (2H, d, J=8.5 Hz), 7.18 (2H, d, J=8.1 Hz), 7.07 (2H, d, J=8.5 Hz), 6.23 (1H, b.s.), 5.00 (1H, b.s.), 4.41 (2H, d, J=6.3 Hz), 4.32 (1H, q, J=7.1 Hz), 3.14 (1H, dd J=13.7, 7.1 Hz), 3.02 (1H, dd, J=13.7, 7.1 Hz), 1.57 (9H, s), 1.41 (9H, s) ppm. $^{13}$C-NMR (125 MHz, $CDCl_3$): δ 171.1, 155.4, 151.9, 150.1, 141.7, 133.9, 130.2, 129.6 (q, J=33.8 Hz), 127.7, 125.6 (q, J=3.7 Hz), 124.0 (q, J=272.9 Hz), 121.5, 53.6, 80.5, 56.0, 42.9, 37.6, 28.2, 27.6 ppm. LRMS (EI): m/z 538 (M+, 0.1), 321 (100), 231 (4), 159 (20), 136 (15).

(2S)-2-[(tert-butoxycarbonyl)amino]-3-[4-(hydroxy) phenyl]-N-[4-(trifluoromethyl) benzyl] propanamide (9)

(9)

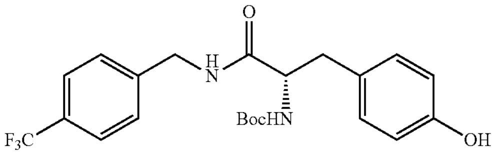

$^1$H-NMR (500 MHz, $CDCl_3$): δ 7.45 (2H, d, J=7.0 Hz), 7.35 (1H, b.s.), 7.11-7.04 (3H, m), 6.93 (2H, d, J=8.3 Hz), 6.65 (2H, d, J=8.3 Hz), 5.56 (1H, b.s.), 4.37 (1H, dd, J=15.5, 6.0 Hz), 4.27-4.14 (2H, m), 2.85 (2H, d, J=7.0 Hz), 1.33 (9H, s) ppm. $^{13}$C-NMR (125 MHz, $CDCl_3$): δ 172.0, 155.6, 152.0, 141.8, 130.2, 129.3 (q, J=34.5 Hz), 127.6, 127.1, 125.2, (q, J=4.2 Hz), 124.0 (q, J=272.0 Hz), 115.3, 80.2, 56.0, 42.6, 37.7, 28.0 ppm. LRMS (EI): m/z 438 (M+, 0.5), 321 (100), 231 (5), 159 (25), 136 (25).

3. Deprotecting Reaction of Boc-Trifluorobenzylaminoacid Derivatives

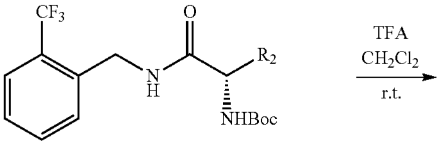

-continued

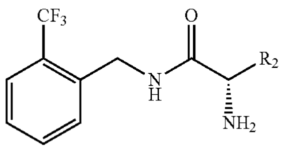

Boc-trifluorobenzylamide derivatives were dissolved in a mixture $CH_2Cl_2$:TFA [2:1] under argon at r.t. and the solution was stirred at this temperature. When the reaction was completed the solvent was removed under reduced pressure. The crude reaction product was purified by two procedures: 1) Procedure A: Reverse phase chromatography using reveleris cartridges SRC C18. 2) Procedure B: Anionic exchange chromatography using Dowex 50WX4 resin followed by silica-gel chromatography.

| Aminoacid | | Procedure | Yield(%) |
|---|---|---|---|
| Lys | 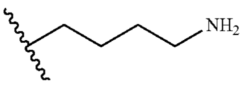 (10) | A | 89% |
| Tyr | 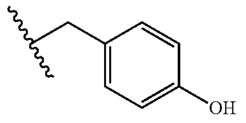 (11-14) | A, B | 86%, 80% |

(2S)-2,6-diamino-N-[2-(trifluoromethyl)benzyl] hexanamide (o-TFB-Lys-TFA)(Procedure A) (10)

10

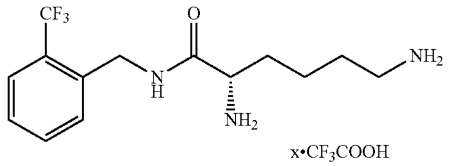

x•$CF_3COOH$ o-TFB-Lys-TFA

$^1$H-NMR (500 MHz, $D_2O$): δ 7.79 (1H, d, J=7.8 Hz), 7.65 (1H, t, J=7.5 Hz), 7.54 (1H, d, J=7.5 Hz), 7.52 (1H, t, J=7.8 Hz), 4.70 (1H, d, J=15.4 Hz), 4.57 (1H, d, J=15.4 Hz), 4.04 (1H, t, J=6.6 Hz), 2.94 (2H, t, J=7.8 Hz), 1.98 (2H, m), 1.72-1.63 (2H, m), 1.43-1.34 (2H, m) ppm. $^{13}$C-NMR (125 MHz, $D_2O$): δ 170.1, 135.4 (q, J=1.7 Hz), 133.2, 130.7, 128.8, 128.1 (q, J=30.7 Hz), 127.0 (q, J=6.0 Hz), 125.0 (q, J=274.4 Hz), 53.6, 41.2 (q, J=2.8 Hz), 39.6, 31.0, 26.9, 21.8 ppm. LRMS (ESI-ES$^+$): m/z 304 $(M+H)^+$, 326 $(M+Na)^+$. IR (KBr): ν 3080, 2882, 2824, 1673, 1433, 1316, 1203, 1128, 1061, 1040, 840, 800, 770, 723 $cm^{-1}$.

(2S)-2-amino-N-[2-(trifluoromethyl)benzyl]-3-[4-(hydroxy)phenyl]propanamide (o-TFB-Tyr-TFA) (Procedure A) (11)

11

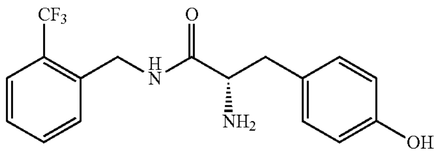

x•$CF_3COOH$ o-TFB-Tyr-TFA

$^1$H-NMR (500 MHz, $CD_3OD$): δ 7.72 (1H, d, J=7.7 Hz), 7.56 (1H, t, J=7.5 Hz), 7.50 (1H, t, J=7.7 Hz), 7.13 (1H, d, J=7.5 Hz), 6.97 (2H, m), 6.66 (2H, m), 4.64 (1H, d, J=15.3 Hz), 4.28 (1H, d, J=15.3 Hz), 4.14 (1H, dd, J=10.0, 5.9 Hz), 3.17 (1H, dd, J=13.6, 5.9 Hz), 2.94 (1H, dd, J=13.6, 10.0 Hz) ppm. $^{13}$C-NMR (125 MHz, $CD_3OD$): δ 167.9, 154.0, 133.6, 131.6, 129.7, 129.5, 127.2, 126.5 (q, J=30.1 Hz), 125.3 (q, J=5.1 Hz), 124.4, 123.4 (q, J=273.6 Hz), 114.8, 53.7, 39.2, 35.2 ppm. LRMS (ESI-ES$^+$): m/z 339 $(M+H)^+$, 361 $(M+Na)^+$, 699 $(2M+Na)^+$. IR (KBr): ν 3416, 3089, 2928, 1677, 1615, 1518, 1439, 1370, 1317, 1204, 1122, 1061, 1041, 840, 801, 770, 723 $cm^{-1}$.

(2S)-2-amino-N-[2-(trifluoromethyl)benzyl]-3-[4-(hydroxy)phenyl]propanamide (0-TFB-Tyr) (Procedure B) (12)

12

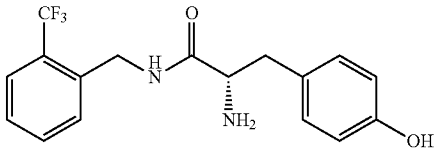

o-TFB-Tyr

$^1$H-NMR (500 MHz, $CDCl_3$): δ 7.69 (1H, t, J=6.1 Hz), 7.63 (1H, d, J=7.6 Hz), 7.50 (1H, dd, J=7.7, 7.4 Hz), 7.43 (1H, d, J=7.7 Hz), 7.37 (1H, dd, J=7.6, 7.4 Hz), 7.02 (2H, m), 6.77-6.74 (2H, m), 4.62 (2H, d, J=6.1 Hz), 3.61 (1H, dd, J=8.8, 4.3 Hz), 3.13 (1H, dd, J=13.8, 4.3 Hz), 2.68 (1H, dd, J=13.8, 8.8 Hz), 3.05 (3H, b.s.) ppm. $^{13}$C-NMR (125 MHz, $CDCl_3$): δ 147.7, 155.2, 136.4, 132.3, 130.6, 130.4, 128.7, 128.2 (q, J=30.6 Hz), 127.6, 126.0 (q, J=6.3 Hz), 124.4 (q, J=274.2 Hz), 115.7, 56.4, 40.0, 39.8 (q, J=2.1 Hz) ppm. LRMS (EI): m/z 321 (34), 231 (25), 159 (56), 136 (100).

(2S)-2-amino-N-[3-(trifluoromethyl)benzyl]-3-[4-(hydroxy)phenyl]propanamide (m-TFB-Tyr) (Procedure B) (13)

13

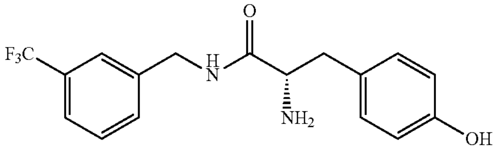

m-TFB-Tyr $^{1}$H-NMR (500 MHz, $CDCl_3$): δ 7.75 (1H, t, J=5.8 Hz), 7.50-7.44 (2H, m), 7.39 (1H, t, J=7.5 Hz), 7.33 (1H, d, J=7.5 Hz), 6.97 (2H, d, J=8.2 Hz), 6.71 (2H, d, J=8.2 Hz), 4.41 (2H, s), 3.58-3.50 (1H, m), 3.04 (1H, dd, J=13.4, 4.2 Hz), 2.86 (3H, b.s.), 2.65 (1H, dd, J=13.4, 9.0 Hz) ppm. $^{13}$C-NMR (125 MHz, $CDCl_3$): δ 174.9, 155.6, 139.0, 130.9 (q, J=1.4 Hz), 130.8 (q, J=32.3 Hz), 130.2, 129.0, 128.0, 124.2 (q, J=3.7 Hz), 124.1 (q, J=3.9 Hz), 123.9 (q, J=272.1 Hz), 115.5, 56.3, 42.5, 40.0 ppm. LRMS (EI): m/z 338 (M+, 0.2), 321 (50), 231 (26), 159 (95), 136 (100).

(2S)-2-amino-N-[4-(trifluoromethyl)benzyl]-3-[4-(hydroxy)phenyl]propanamide (p-TFB-Tyr) (Procedure B) (14)

14

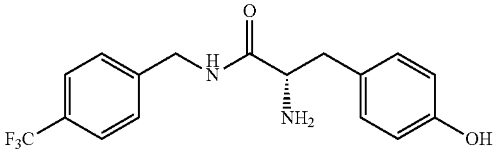

p-TFB-Tyr $^{1}$H-NMR (500 MHz, $CDCl_3$): δ 7.75 (2H, J=5.6 Hz), 7.50 (2H, d, J=8.0 Hz), 7.22 (2H, d, J=8.0 Hz), 6.96 (2H, d, J=8.4 Hz), 6.70 (1H, d, J=8.4 Hz), 4.39 (2H, s), 3.51 (1H, dd, J=8.3, 5.0 Hz), 3.10 (3H, s), 3.00 (1H, dd, J=13.8, 5.0 Hz), 2.66 (1H, dd, J=13.8, 8.3 Hz) ppm. $^{13}$C-NMR (125 MHz, $CDCl_3$): δ 174.9, 155.7, 142.0 (q, J=1.4 Hz), 130.2, 129.4 (q, J=33.6 Hz), 127.9, 127.6, 125.4 (q, J=5.4 Hz), 124.0 (q, J=272.1 Hz), 115.4, 56.3, 42.4, 40.0 ppm. LRMS (EI): m/z 338 (M+, 0.2), 321 (44), 231 (25), 159 (85), 136 (100) 107 (33).

Functional and Pharmacological (ADME) Assays

Effect of the Interaction with the Target Molecule.

Functional (Biological) Tests.

In vitro cytotoxicity analysis based on the MTT assay was performed to confirm the desired biological effect of the new small molecular mass compounds on the cancer cells. A total of 45 unique molecules were tested using a triple-negative breast cancer cell line (HCC38), because in this cancer cell line Cdc20 is known to be amplified.

Set 1 results. The lead compound (o-TFB-Tyr) was tested at 25 and 5 uM alone and in combination with the APC/C antagonist proTAME. The reported Cdc20 inhibitor apcin was used for comparison (see FIG. 2).

Set 2 results. The lead compound (o-TFB-Tyr) was tested in the 5 uM to 100 nM concentration range alone and in combination with the APC/C antagonist proTAME. The reported Cdc20 inhibitor apcin was used for comparison (see FIG. 3).

Figure 2:
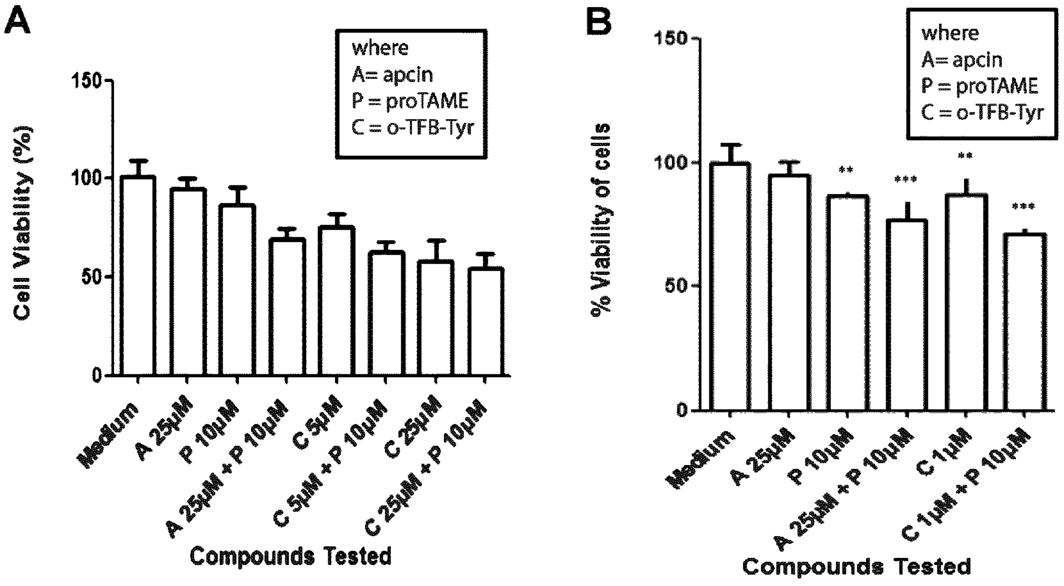
FIG. 2. Shows the cytotoxic analysis by the MTT assay of compounds tested against triple negative breast cancer cells, using Cdc20 inhibitor apcin for comparison. Cytotoxic analysis of non-synchronised HCC-38 triple negative breast cancer cells after 24 hours treatment with selected third-generation Compound o-TFB-Tyr. The HCC-38 cells were exposed to Compound o-TFB-Tyr at 25 μM and 5 μM concentration (Panel A) and at 1 μM concentration (Panel B) alone and in combination with proTAME. Negative control used was untreated cells (medium), while positive controls used were Apcin 25 μM and proTAME 10 μM alone and Apcin 25 μM combined with proTAME 10 μM. Data was analysed by One-way analysis of variance and Dunnett Test, with all columns compared to negative control column (medium), $p<0.001$. Replicate experiments were performed.
Figure 3:
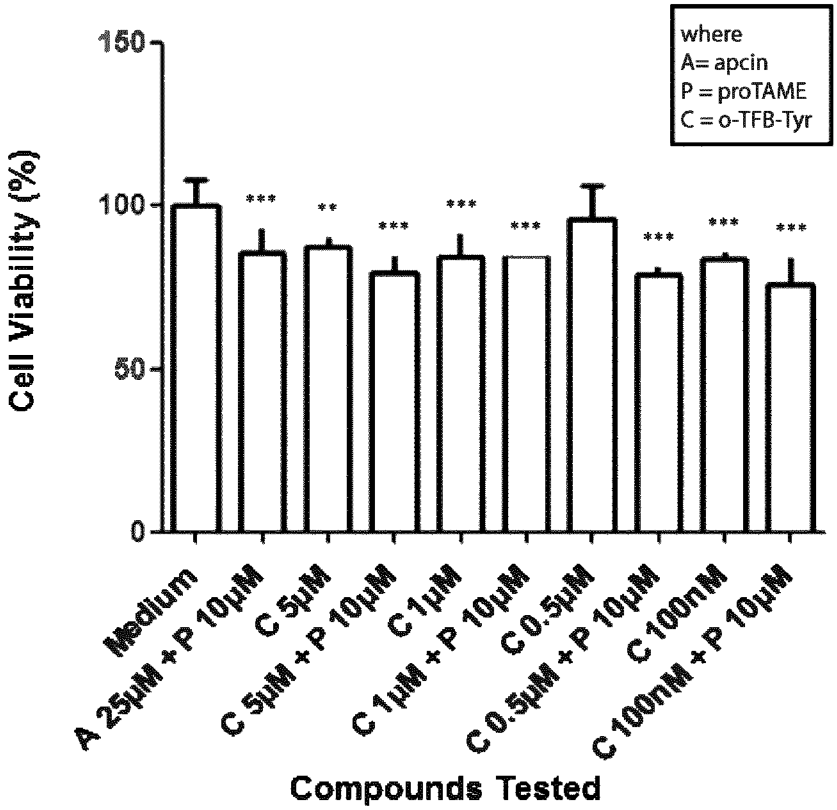
FIG. 3. Shows the cytotoxic analysis of compound o-TFB-Tyr at 5 μM, 1 μM, 0.5 μM and 100 nM concentration. HCC-38 cancer cells were exposed to Compound o-TFB-Tyr alone and in combination with proTAME. Negative control used was untreated cells (medium), while positive control used was Apcin 25 μM combined with proTAME 10 μM. Data was analysed by One-way analysis of variance and Dunnett Test, with all columns compared to negative control column (medium), $p<0.001$. Replicate experiments were performed.
Figure 4:
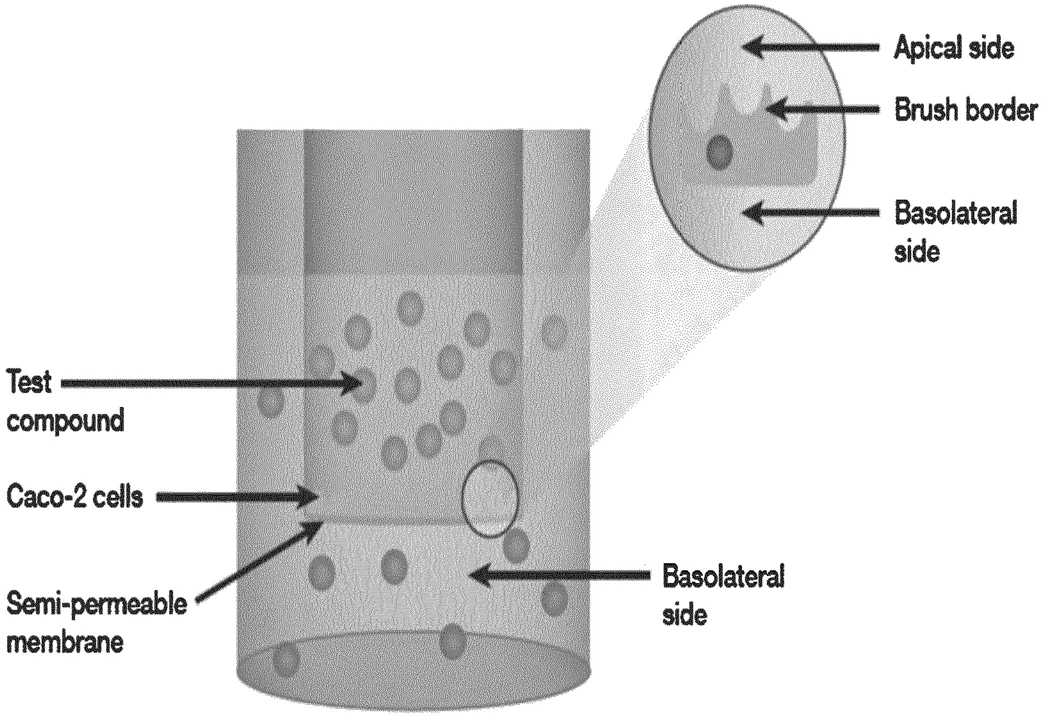
FIG. 4. Shows the principle of the cell membrane permeability test that formed part of the ADME studies.

From the functional studies summarized in FIGS. 2 and 3, one compound (o-TFB-Tyr) was selected for pharmacological tests, including cell permeability (FIG. 4).

Pharmacological studies. These included determination of ADME (Adsorption, Distribution, Metabolism and Excretion) assays of o-TFB-Tyr. The results of these tests are summarised as follows:

Kinetic solubility. This is a valuable initial screen that was carried out prior to starting ADME test in order to identify potential issues and to determine appropriate concentration ranges. Kinetic solubility was measured using a turbidimetric method. The results of this test are shown in Table 1 below:

TABLE 1

| Estimated Precipitation Range (μM) | | |
|---|---|---|
| Lower bound | Upper bound | Calculated mid-range |
| 100 | >100 | >100 |

This data demonstrated that o-TFB-Tyr is readily soluble in aqueous solutions.

Adsorption

This was determined using an intestinal permeability assay in Caco-2 cells, a human colorectal adenocarcinoma cell line (see FIG. 4).

The results of this test are shown on table 2 below:

TABLE 2

| Caco2 permeability dynamic | | | | |
|---|---|---|---|---|
| Direction A to B | | Direction B to A | | Efflux ratio (Mean Papp B to A/Mean Papp A to B) |
| Mean Papp ($10^{-6}$ $cm^{-1}$) | Mean % recovery | Mean Papp ($10^{-6}$ $cm^{-1}$) | Mean % recovery | |
| 22.1 | 62.8 | 19.1 | 88.9 | 0.862 |

and indicate the compound diffuses freely across the semipermeable membrane in both directions. This in turn indicates the compound is not actively transported by membranes proteins such as ABC transporters, which may have limited its use as a drug.

Distribution, Metabolism and Excretion

Metabolic Stability Test

The liver is the major drug metabolising organ for the large majority of pharmaceutical drugs. A good in vitro model to investigate drug metabolism is based on the use of microsomes, a subcellular fraction of the liver.

The results from this test are shown on table 3 below and demonstrated the compound was stable, with 8% of the intact molecule present after 45 minutes.

TABLE 3

| Metabolic stability (Species = Human, Has QCs = No) | | | | | | | |
|---|---|---|---|---|---|---|---|
| Compound remaining (% of 0 min) 0 min | 5 min | 15 min | 30 min | 45 min | Control | Supplier Test ID | Control group ID |
| 100 | 107 | 43.7 | 19.3 | 8.23 | 89.8 | 5212854 | 146078_1 |

Drug Clearance

Two thirds of drugs cleared by metabolism are metabolised at least in part by the cytochrome P450 (CYP) enzymes with the isoform CYP3A4 accounting for almost 50% of all CYP activity. For this reason, we tested whether CYP3A4 is implicated in the clearance of o-TFB-Tyr. Table 4 below show Cytochrome P450 (CYP3A4 isoform) inhibition ($IC_{50}$) determination. The possible inhibition of CYP3A4 by the lead compound (o-TFB-Tyr) was tested using midazolam and testosterone as the CYP3A4 substrates.

TABLE 4

Cytochrome P450 inhibition $IC_{50}$ determination (isoform CYP3A4)

| % inhibition with substrate imidazole 0 µM | 0.1 µM | 0.25 µM | 1 µM | 2.5 µM | 10 µM | 25 µM |
|---|---|---|---|---|---|---|
| 0 | 13.70 | 22.50 | 47.50 | 65.60 | 84.40 | 91.10 |
| **% inhibition with substrate testosterone 0 µM** | **0.1 µM** | **0.25 µM** | **1 µM** | **2.5 µM** | **10 µM** | **25 µM** |
| 0 | −0.990 | 0.136 | 4.210 | 49.0 | 77.30 | 89.50 |

In both cases, the $IC_{50}$ was much higher than that of controls compounds that are known to be metabolised by the cytochrome P450 isoform CYP3A4. For the purpose of comparison, the data of the control compound (ketoconazole) using midazolam and testosterone are shown in table 5 below:

TABLE 5

Cytochrome P450 inhibition $IC_{50}$ determination controls (group 146243_4)

| | $IC_{50}$ (µM) | SE (µM) | n | Supplier Test ID | Variables |
|---|---|---|---|---|---|
| With midazolam as the substrate | | | | | |
| Control compound Ketoconazole (top compound concentration = 3 µM) | 0.0933 | 0.00562 | 7 | 5218881 | Isoform CYP3A4 |
| With testosterone as the substrate | | | | | |
| Control compound Ketoconazole (top compound concentration = 3 µM) | 0.231 | 0.0535 | 7 | 5212280 | Isoform CYP3A4 |

Taken together, the data shown in Tables 4 and 5 suggest that the cytochrome P450 isoform CYP3A4 seems to play a marginal role in the clearance of o-TFB-Tyr. However, further studies are required to confirm these observations.

Plasma Protein Binding Assay

Non-specific plasma protein binding can greatly affect the extent of free drug concentration which may influence the lead compound's subsequent inhibitory potential (see table 6 below).

TABLE 6

Protein binding (protein type = plasma spiked 1 side; species = human)

| Fraction unbound Replicate 1 | Replicate 2 | Replicate 3 | Mean fraction unbound | SD | n | Mean % recovery |
|---|---|---|---|---|---|---|
| 0.352 | 0.328 | 0.304 | 0.328 | 0.0236 | 3 | 101 |

Protein binding (protein type = plasma spiked 1 side; species = mouse)

| Fraction unbound Replicate 1 | Replicate 2 | Replicate 3 | Mean fraction unbound | SD | n | Mean % recovery |
|---|---|---|---|---|---|---|
| 0.280 | 0.280 | 0.301 | 0.287 | 0.0119 | 3 | 102 |

In both cases (human and mouse), total recovery of the protein was observed, indicating the absence of non-specific plasma protein binding.

Cytotoxicity Results

Key Results

Figure 5:
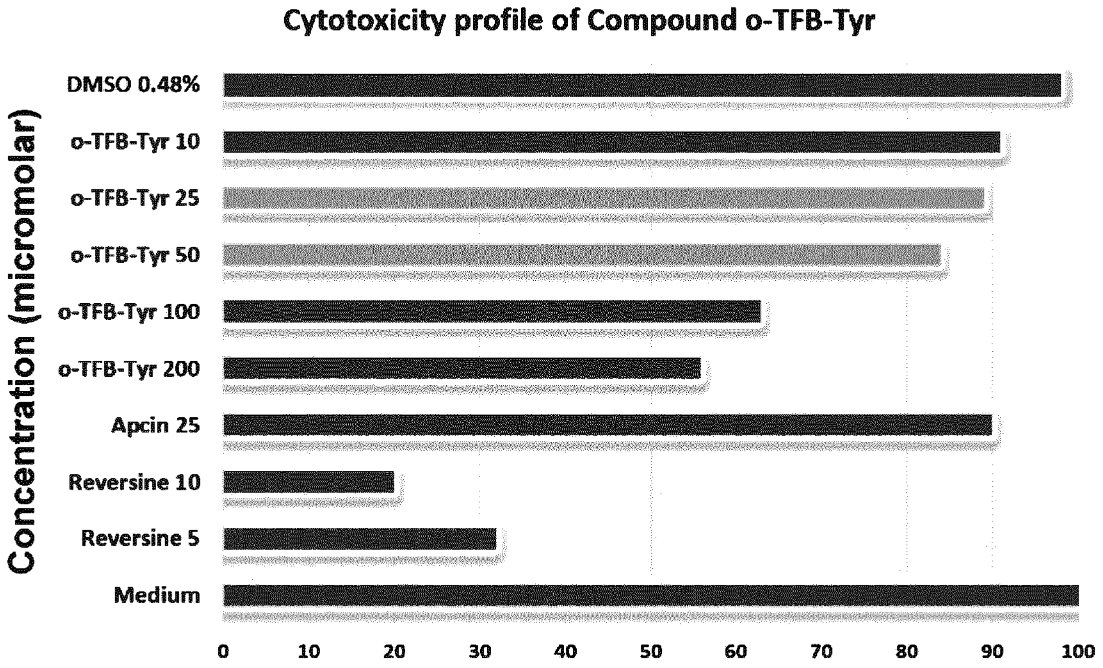
FIG. 5. Graph showing the relative cytotoxicity of Compound o-TFB-Tyr at different concentrations in HeLa cells compared to Reversine a small compound inhibitor of Mps1 kinase, an upstream regulator of the SAC and Apcin, a small size binder of Cdc20 and inhibitor of APC/C activation by Cdc20. The study confirmed the compound o-TFB-Tyr exhibited the higher cytotoxic effect against different types of cancer of diverse tissue origin.
Figure 6:
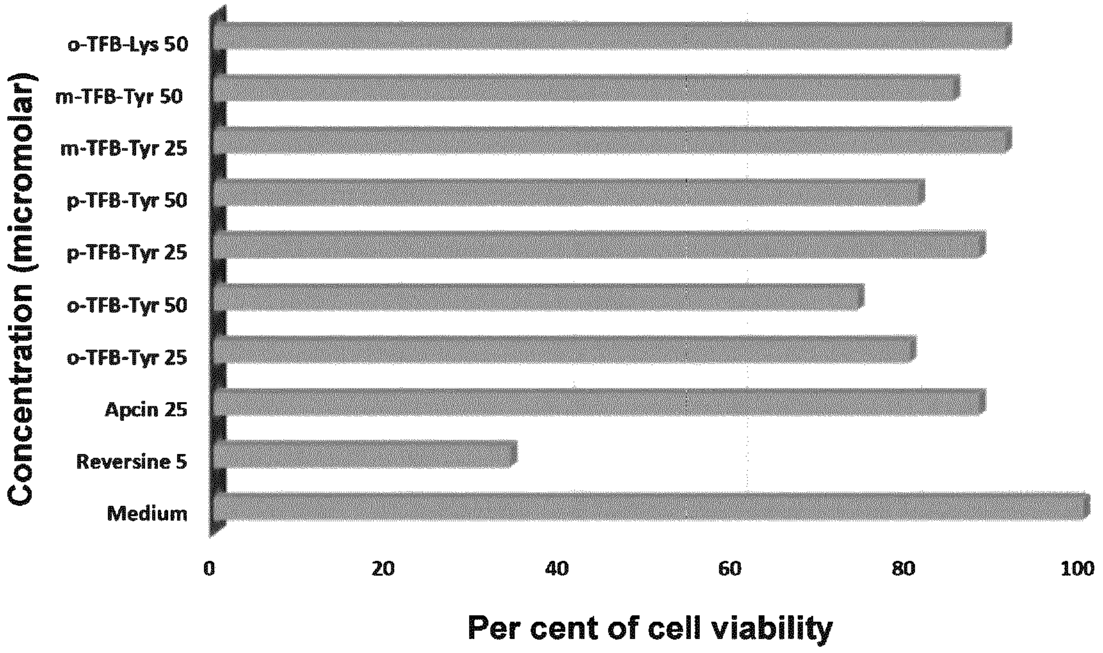
FIG. 6. Comparison of the relative cytotoxicity of Compound o-TFB-Tyr in HeLa cells was compared to compounds Apcin, m-TFB-Tyr, p-TFB-Tyr, and o-TFB-Lys, at the same concentrations. Compounds o-TFB-Tyr, m-TFB-Tyr, and p-TFB-Tyr are closely related in terms of chemical structure. The comparative study confirmed the compound o-TFB-Tyr exhibited the higher cytotoxic effect against cancer cells in culture. Hence, revealing the key stereochemical features of o-TFB-Tyr and the isomers m-TFB-Tyr, p-TFB-Tyr that account for the anticancer activity of o-TFB-Tyr and structurally related molecules. The comparative analysis also showed that the chemical nature of R2 residues of the claimed compounds o-TFB-Tyr, m-TFB-Tyr, p-TFB-Tyr, and o-TFB-Lys account for the cancer cells cytotoxicity of these molecules.
Figure 6:
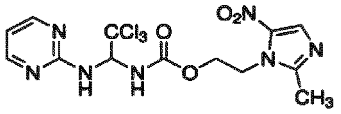
Figure 6:
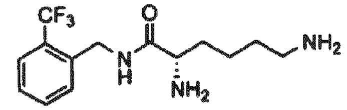
Figure 6:
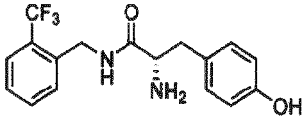
Figure 6:
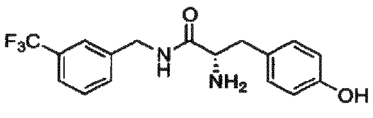
Figure 6:
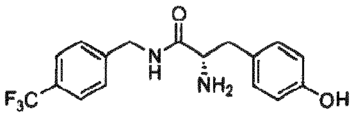

Cytotoxicity and clonogenic studies conducted in HeLa cells confirm the moderate cytotoxic activity (that is, in the range 200 to 10 µM) of compound o-TFB-Tyr in this cancer cell line. The cytotoxicity effect observed in HeLa cells (shown in FIGS. 5 and 6) was comparable to that determined in the triple negative breast cancer cell line HCC-38. Moreover, western blot analysis of HCC-38 cells treated with Compound o-TFB-Tyr confirmed the inhibitory effect of this compound on APC/C activation by Cdc20, as monitored by inhibition of Cyclin B, a substrate of the APC/C E3 ubiquitin ligase. The cytotoxicity of a series of compounds that are structurally related to the compound o-TFB-Tyr was also tested in both HCC-38 and HeLa cells, confirming that certain stereochemistry features of compound o-TFB-Tyr have an important effect on the desired biological activity of this compound.

Methodology

Cell Growth

The entirety of the following protocol was carried out under aseptic conditions. HeLa cells were cultured in Dulbecco's Modified Eagle's Medium (DMEM) supplemented with 10% Fetal Bovine Serum (FBS) (Sigma F7524). Cells were counted and seeded into clear bottom 96-well plates (Greiner Bio-One) at density 6,000 cells/well. 100 µl of cells were added to each well and placed in the incubator overnight. The following day medium was aspired and 100 µL of treatment was added to wells. Cells were treated with controls (medium alone, Reversine 5 µM, Apcin 25 µM). All stock solutions of Apcin and compounds were prepared by resuspension of the solid in Dimethyl Sulfoxide (DSMO), then diluted in medium to achieve concentration of 200 µM, then diluted again in medium to the final concentrations being tested.

Cytotoxicity Analysis

In vitro cytotoxic analysis involved quantitative measurements of cell proliferation and the subsequent assessment of the relative toxicity of the compounds. (3-(4,5-Dimethylthiazol-2-yl)-2,5-Diphenyltertrazolium Bromide (MTT) is a widely utilised cytotoxic assay that measures cellular metabolic activity as an indicator for cell viability, proliferation and cytotoxicity from the reduction of water soluble yellow tetrazole MTT to insoluble purple formazan crystals by mitochondrial dehydrogenases. The insoluble purple crystalline product was dissolved in DMSO and the resulting coloured solution quantified by measuring the absorbance (570 nm). Reduction can only occur when mitochondrial reductive enzymes are active, thus a direct correlation to the number of viable cells. Comparison of purple formazan produced by cells treated with compounds to untreated control cells, enabled the cytotoxicity of the compound to be ascertained with % cell viability calculated. Treatments tested were performed in triplicate.

Cells were incubated and had 72 hours treatment exposure; 3 hours before end of exposure 5 µl of MTT (5 mg/ml) (Invitrogen M6494) was added to each well, then plates placed in the incubator for the remaining treatment exposure time. Solution from each well was aspired, then 100 µl of DMSO added to wells and plates placed on a shaker for 15 minutes at room temperature. Once a homogenous colour was visible for each well, absorbance was measured (570 nm) (Spectramax i3x). Cytotoxic readings for treated cells were normalised to the negative control (medium alone) and from the following equation % viability of cells was calculated:

$$\text{Viability of cells (\%)} = \left(\frac{\text{Absorbance of sample} - \text{Blank}}{\text{Absorbance of negative control} - \text{Blank}}\right) * 100$$

Data was analysed by One-way Analysis of Variance (ANOVA) and post hoc Dunnet test using GraphPad Prism 7.0, GraphPad Software, Inc. For data obtained all treatments were compared to control (medium alone), $p<0.001$.

Clonogenic Assays

Figure 7:
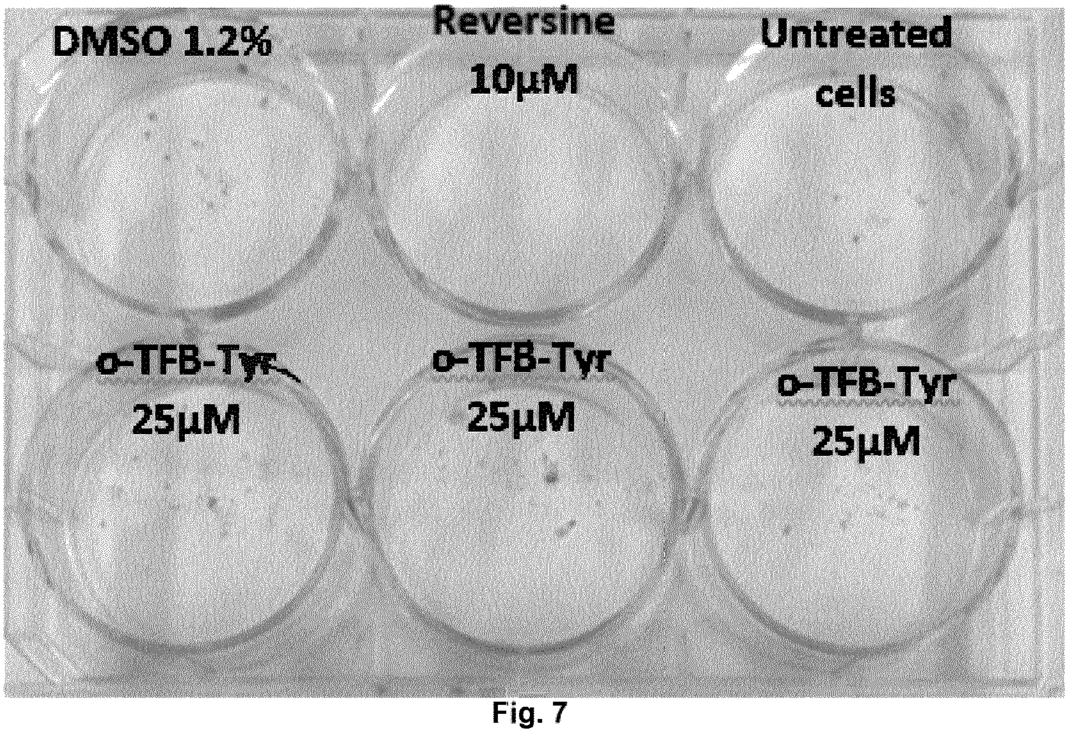
FIG. 7. Clonogenic assay of HCC-38 cells treated with DMSO (1.2% v/v), the Mps1 kinase inhibitor Reversine, the Cdc20 binder Apcin and compound o-TFB-Tyr. The clones were stained after 12 days incubation at 37 Celsius. Following treatment of the HCC38 cells with the compounds for 24 hours, the medium was exchanged every 48 hrs. In this assay, a lower number of triple negative breast cancer cell clones was consistently observed in the cells treated with Reversine and o-TFB-Tyr, confirming the desired cytotoxic activity of the latter compound in cancer cells.

The entirety of the following procedure was carried out under aseptic conditions. HeLa cells were counted and seeded into clear bottom 6-well plates (Greiner Bio-One) at density 500 cells/well (250 cells/ml). 2 ml of cells were added to each well and placed in the incubator (37° C., 5% $CO_2$) overnight. The following day medium was aspired and 1.5 ml of treatment was added to wells. Cells were treated with control (medium alone) and compounds. All stock solutions of compounds were prepared by resuspension of the solid in DMSO, then diluted in medium to the final concentrations being tested. HeLa cells viability was measured using clonogenic assay, a cell survival-based assay that determines cell reproductive death after treatment with cytotoxic agents. Cells were incubated and had 72 hours treatment exposure. Solution from each well was then aspired, and 2 ml of medium added to wells and plates placed back in the incubator. Plates were incubated for 9 more days (10 days in total), with cells washed with 1×PBS and 2 ml medium in each well replaced with 2 ml of fresh medium every few days. After 10-day incubation from when treatment was added, solution from each well was aspired and cells washed twice with 1×PBS. 500 µl of 4% Paraformaldehyde in PBS (Alfa Aesar J61899) was then added to each well and plates incubated at room temperature for 30 minutes. Solution from each well was aspired, then 4-5 drops of crystal violet (0.5% w/v in methanol) added to each well. Plates were incubated at room temperature for 15 minutes. Solution was gently removed by washing each well with water and clones visualised. A representative image of the clonogenic assay results is shown in FIG. 7.

Figure 8:
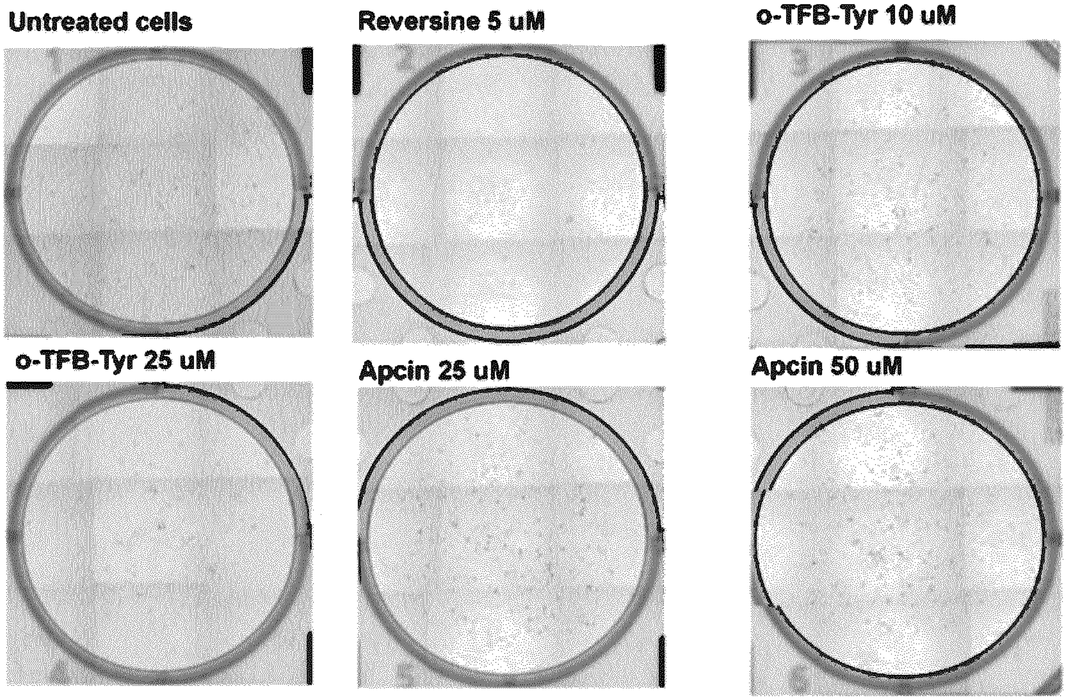
FIG. 8. Each well of the clonogenic assay was then scanned using an Axiozoom Zeiss Axioplan fluorescence microscope equipped for DIC imaging and fluorescence imaging and analysed using the ImageJ2 image-processing software (Fiji). A representative picture generated by the image processing software is shown here.

Each well of the clonogenic assay was then scanned using an Axiozoom Zeiss Axioplan fluorescence microscope equipped for DIC imaging and fluorescence imaging and analysed using the ImageJ2 image-processing software (Fiji). A representative picture generated by the image processing software is shown below (FIG. 8).

Figure 9:
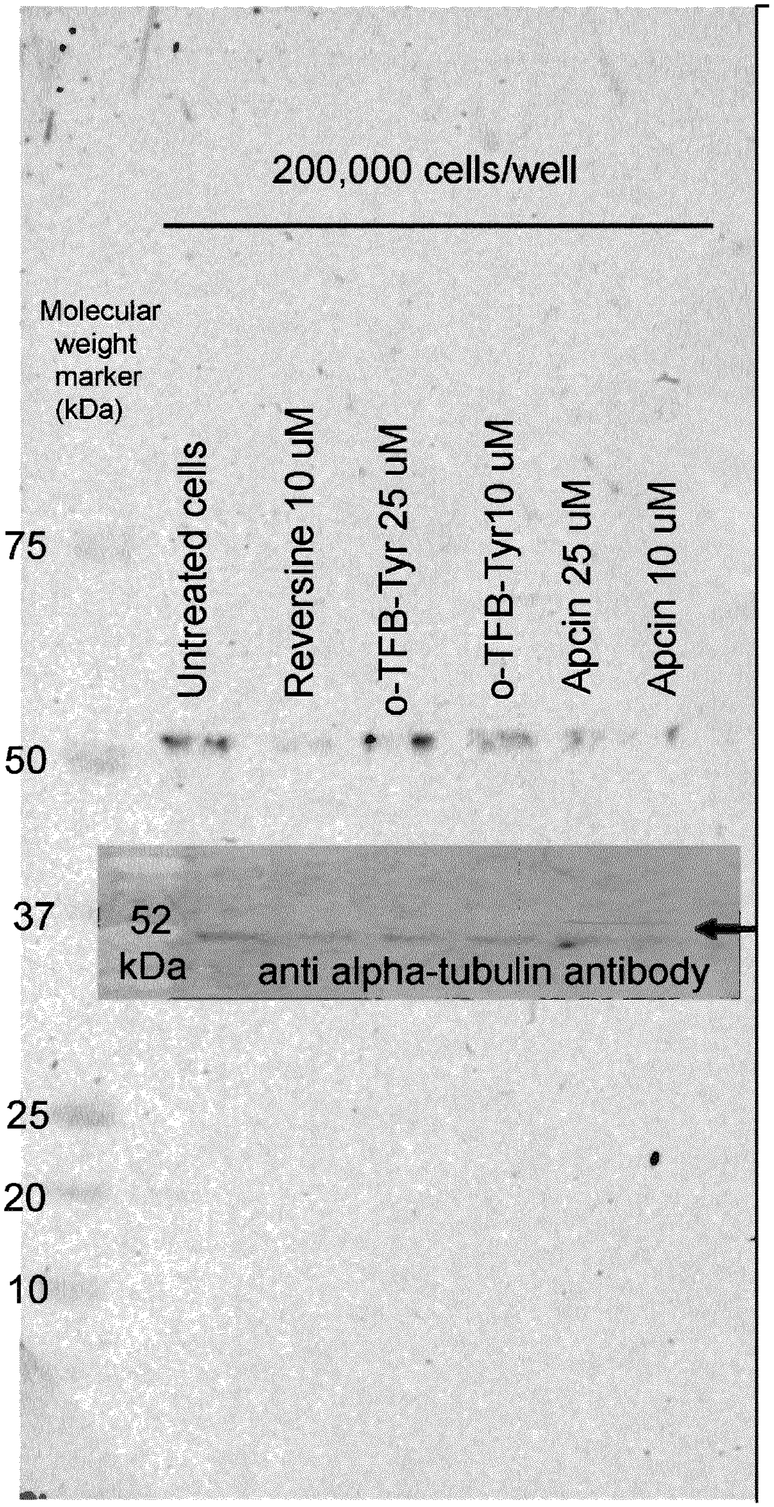
FIG. 9. Western blot showing that Compound o-TFB-Tyr causes inhibition of Cyclin B ubiquitylation by APC/C. Consequently, non-ubiquitylated Cyclin B escapes degradation by the proteasome. This analysis also shows that Apcin was comparatively less effective than compound o-TFB-Tyr as antagonist of APC/C activation by Cdc20. HCC-38 cells at a density of 200,000 cells per well were used in this study.

Confirmation of Inhibition of APC/C Activation by Cdc20 by Measuring Cyclin B1 Levels The entirety of the following procedure was carried out under aseptic conditions. HeLa cells were counted and seeded into clear bottom 6-well plates (Greiner Bio-One) at a density of 200,000 cells/well in a volume of 2 ml and placed in an incubator (37° C., 5% $CO_2$) overnight. The following day medium was aspired and 1.5 ml of treatment was added to wells. Cells were treated with controls (medium alone) and compounds. All stock solutions of the small compounds were prepared by resuspension of the solid in DSMO, then diluted in medium to the final concentrations being tested. The effect of these compounds on mitosis was analysed by measuring Cyclin B1 levels, a downstream target of APC/C-Cdc20. Cells were incubated and had 24 hours treatment exposure. Plates were then placed on ice and solution from each well was aspired. Cells were washed twice with PBS, then 300 µl of Lysis Buffer (50 mM Tris pH 8, 150 mM NaCl, 5 mM ETDA, 1% Triton X-100, 5 mM Re, Deoxyribonuclease I from bovine pancreas, cOmplete Mini EDTA-free protease inhibitor cocktail tablets (1 tablet/50 ml of lysis) was added to each well and plates incubated for 10 minutes with agitation. Using a cell scraper each well was scraped for 2 minutes then the solution for each well transferred into corresponding labelled Eppendorf tubes. The tubes were then centrifuged at 14,500 rpm, 4° C. for 30 minutes. The supernatant from each tube was transferred to clean Eppendorf tubes, flash frozen and stored at −20° C. FIG. 9 shows a western blot of HCC-38 cells treated with Compound o-TFB-Tyr, which confirmed the inhibition of APC/C activation by Cdc20, as monitored by inhibition of Cyclin B. Mouse Anti-Cyclin B1 antibody (BD Pharmingen 554177) was used as the primary antibody. Anti-Mouse IgG AP-linked was used as the secondary antibody (Sigma SAB3701107-1). Mouse anti α-tubulin antibody (Santa Cruz Biotechnology sc-32293) was used as an internal control of protein concentration loading.

The invention claimed is:

1. A compound of formula I:

Formula I

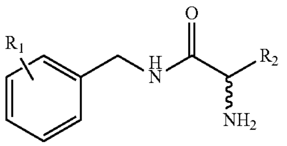

or a pharmaceutical salt thereof, wherein:

$R_1$ represents —$CF_3$;

$R_2$ represents $C_1$-$C_6$ alkyl substituted $Cy_1$;

$Cy_1$ represents a phenyl group (-Ph) substituted by —OH.

2. The compound of formula I or a pharmaceutical salt thereof according to claim 1, wherein $Cy_1$ represents a phenyl group (-Ph) substituted by —OH in para-position.

3. The compound of formula I or a pharmaceutical salt thereof according claim 1, wherein $R_2$ is a group of formula $R_2$-a:

$R_2$-a

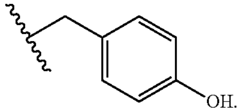

4. The compound of formula I or a pharmaceutical salt thereof according to claim 1, wherein the compound of formula I is selected from:

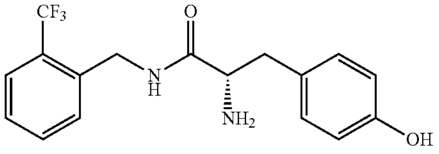

o-TFB-Tyr

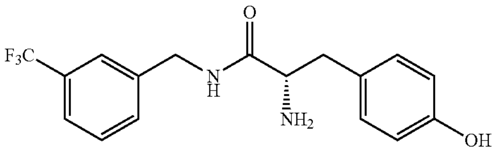

m-TFB-Tyr

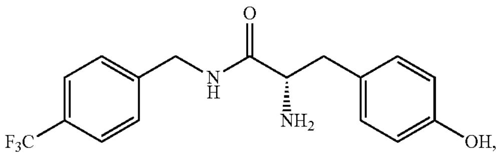

and p-TFB-Tyr

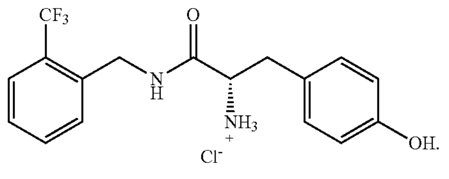

o-TFB-Tyr-Cl

5. The compound of formula I or a pharmaceutical salt thereof according to claim 4, wherein the compound of formula I is:

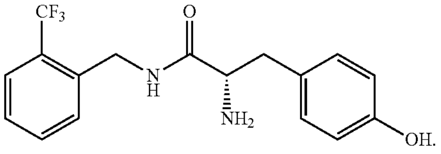

o-TFB-Tyr

6. A pharmaceutical composition which comprises a compound of formula I according claim 1 or a pharmaceutically acceptable salt thereof andone or more pharmaceutically acceptable excipients.

7. A pharmaceutical composition comprising a compound of formula I according to claim 1, in combination with a further compound selected from pro-N-4-tosyl-L-arginine methyl ester (proTame).

8. A method for the treatment of cancer comprising administering to a subject in need thereof an effective amount of a compound of formula I:

Formula I

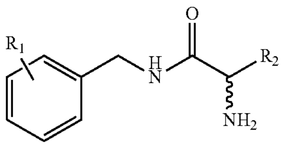

or a pharmaceutical salt thereof, wherein:

$R_1$ represents —$CF_3$;

$R_2$ represents $C_1$-$C_6$ alkyl substituted $Cy_1$;

$Cy_1$ represents a phenyl group (-Ph) substituted by —OH, and wherein the cancer is breast cancer.

9. The method according to claim 8, wherein the compound of formula I is selected from:

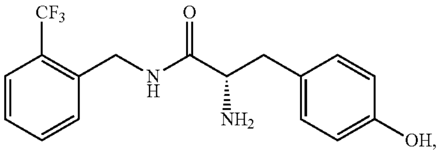

o-TFB-Tyr

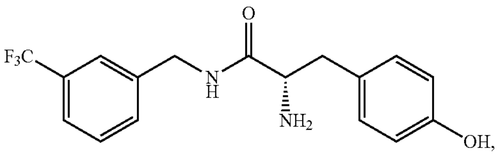

m-TFB-Tyr

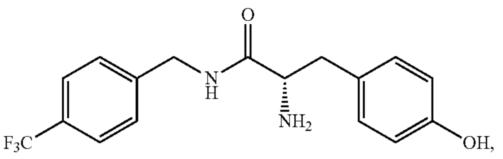

and p-TFB-Tyr

-continued
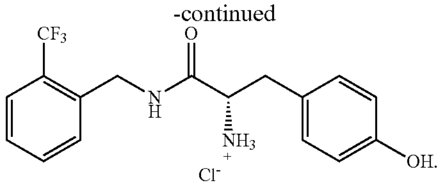
o-TFB-Tyr-Cl
10. The method according to claim 8, wherein the compound of formula I is:
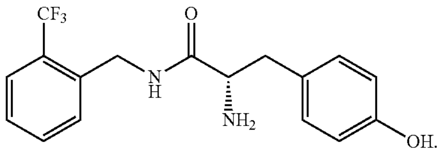
o-TFB-Tyr
* * * * *